United States Patent [19]

Bhat et al.

[11] Patent Number: 4,800,076

[45] Date of Patent: Jan. 24, 1989

[54] SKIN CARE COMPOSITIONS

[75] Inventors: Gulgunji R. Bhat, Ringoes; Elvin R. Lukenbach, Somerset; Ralph C. Stutzman, Ringoes, all of N.J.

[73] Assignee: Johnson & Johnson Consumer Products, Inc., New Brunswick, N.J.

[21] Appl. No.: 25,453

[22] Filed: Mar. 13, 1987

[51] Int. Cl.$^4$ .................. A61K 7/35; A61K 47/00
[52] U.S. Cl. ...................................... 424/69; 514/770
[58] Field of Search ............... 424/69, 400, 484, 489, 424/357

[56] References Cited

U.S. PATENT DOCUMENTS

| | | | |
|---|---|---|---|
| 2,838,440 | 6/1958 | Thurmon | 424/69 |
| 2,987,447 | 6/1961 | Ward | 424/69 |
| 3,800,034 | 3/1974 | Kricher et al. | 424/69 X |
| 3,801,709 | 4/1974 | Augsburger et al. | 424/69 |
| 4,087,517 | 5/1978 | Scott | 424/69 |
| 4,137,302 | 1/1979 | Humbert et al. | 424/69 X |
| 4,185,086 | 1/1980 | Meitz | 424/69 |
| 4,272,514 | 6/1981 | Spence | 424/69 |
| 4,485,092 | 11/1984 | Ashton et al. | 424/69 |
| 4,591,502 | 5/1986 | Schlossman | 424/69 X |
| 4,650,672 | 3/1987 | Yagita et al. | 424/69 |

*Primary Examiner*—Nancy A. B. Swisher
*Attorney, Agent, or Firm*—Steven P. Berman

[57] ABSTRACT

The present invention relates to skin care compositions with improved aesthetic and physical characteristics comprising a lotion, cream or anhydrous base and talc with specific ratios of the non-volatile ingredients to talc.

8 Claims, No Drawings

SKIN CARE COMPOSITIONS

BACKGROUND OF THE INVENTION

The present invention relates to skin care compositions. More particularly, the present invention relates to skin care compositions with improved aesthetic and physical characteristics.

A soft, supple and flexible skin has a marked cosmetic appeal and is an attribute of normal functioning epidermis. The outer layer of the epidermis, the stratum corneum, can, however, become dry and flaky following exposure to adverse climatic conditions or excessive contact with detergents or solvents which result in the loss of skin moisturization with the further result that the skin loses its soft, supple and flexible characteristics. Various emollients such as fats, phospholipids and sterols have been utilized in various products to soften dry skin with varying degrees of success. Many of these products in lotion, cream or anhydrous format have not been perceived as cosmetically elegant by the consumer. The term "cosmetically elegant" can be used to describe a product which is attractively appearing, is non-greasy, non-tacky, has good skin feel, is spreadable and smooth.

Skin care products in lotion, cream and anhydrous format have always contained non-volatile oils and/or mixtures of non-volatile oils for their skin conditioning properties but many of these products have therefore been lacking in some of the above described cosmetic properties desired by some consumers, in particular, the non-greasy characteristic.

SUMMARY OF THE INVENTION

It is an object of the present invention to provide improved skin care compositions.

It is a further object of this invention to provide skin care compositions with improved aesthetic and physical characteristics.

Other objects of the invention will be set forth in or be apparent from the following detailed description of the invention.

The foregoing objects and other features and advantages of the present invention are achieved by a skin care composition containing talc wherein the talc and other non-volatile ingredients are within specific ratios.

DETAILED DESCRIPTION OF THE INVENTION

According to the present invention, it has been found that talc in combination with conventional non-volatile ingredients found in lotion, cream and anhydrous skin care compositions in specific ratios, provides improved cosmetically-acceptable skin care compositions.

Skin care compositions, either lotions, creams or anhydrous formulations, can be prepared in accordance with the present invention from numerous cosmetic base ingredients which are well known in the art. If a lotion or cream formulation is desired, such bases may comprise emulsions containing various emollient ingredients. There is considerable variation in the specific formulations making up the oil and water phases of such preparations.

Mineral oils, animal oils, vegetable oils and silicones have all been used in cosmetic creams and lotions of the emulsion type. In addition to such oils, other emollients and surface active agents have been incorporated in the emulsions, including stearates, such as potassium stearate, glycol stearate, sodium stearate, polyethylene glycol (40) stearate and glyceryl stearate; laurates, such as sodium laurate and potassium laurate; alcohols, such as cetyl alcohol and lanolin alcohol; triethanolamine; myristates, such as isopropyl myristate, sodium myristate and potassium myristate; cetyl palmitate; cholesterol; stearic acid; sorbitan sesquioleate; propylene glycol; glycerine, sorbitol and the like. Stabilizers, such as butylated hydroxytoluene, thickeners such as natural gums and synthetic polymers, as well as preservatives such as methylparaben and propylparaben, coloring agents and fragrances also are commonly included in such compositions.

If an anhydrous formulation is desired, these can also be prepared utilizing well-known base ingredients. By the term "anyhdrous formulation", it is meant to encompass all skin care compositions that do not contain water. The base ingredients include the non-volatile oils and waxes normally found in such compositions including mineral oils, petroleum, mineral waxes, hydrogenated fats including both vegetable and animal fats, vegetable and animal waxes and lanolin, synthetic waxes, fatty alcohols, phospholipids, silicone oils and waxes and inert fillers. Other well-known ingredients such as the previously discussed stabilizers, preservatives, coloring agents and fragrances can also be included in such compositions.

The essence of the present invention is not within the composition of the base per se and any of the many formulations or compositions of the lotion, cream or anhydrous type currently utilized in skin care preparations can be employed. The essence of the present invention is in the incorporation of talc within the lotion, cream or anhydrous base preparation in a specific ratio based on the amount of non-volatile ingredients contained in said preparations. When the term "non-volatile ingredients" is used herein, it is meant to include all non-volatile ingredients in a composition except talc. The incorporation of talc in specific ratios with the non-volatile materials in such base compositions substantially and markedly enhances the desired characteristics of the resulting skin care compositions. These compositions are less greasy, have a faster "rub-in", i.e. the perceived absorption of the composition into the skin, and result in a "silky" and smooth afterfeel with "talc-like" dry lubricity characteristics.

The talc which is useful in the present invention is a cosmetic grade of talc which conforms to the Cosmetic Toiletry and Fragrance Association, Inc. specifications. Such talc is essentially a white, odorless, fine powder ground from a naturally occurring rock ore and it typically consists of about 90% hydrous magnesium silicate having a structural formula of $Mg_6(Si_8O_{20})$—$(OH)_4$ with the remainder consisting of naturally associated minerals such as calcite, chlorite, dolomite, kaolin and magnesite and containing no asbestos minerals. The preferred particle size is such that 100% passes through a 60 mesh screen and not less than 99% passes through a 100 mesh screen and at least 98% passes through a 200 mesh screen.

The ratio of non-volatile ingredients to talc in the skin care compositions of the present invention should be from about 0.4:1 to 3.2:1, preferably from about 0.6:1 to 2.0:1 and most preferably from about 1.0:1 to 1.4:1. The actual amount of talc as a weight percent of the total composition will vary depending on the amount by weight of the non-volatile materials in any particular base formulation. For example, in a lotion formulation, the amount of talc would generally be in the range of from about 5 to 30% by weight of the total composition.

The compositions of the present invention can be prepared by well-known mixing or blending procedures and demonstrate reduced greasiness, faster rub-in and good afterfeel and lubricity. Furthermore, it has been found that when the amount of talc added is within the required ratios, it results in the compositions maintaining their desired color and upon utilization on the skin exhibiting no visible talc residue.

Specific embodiments of the skin care compositions prepared in accordance with the present invention are illustrated by the following representative examples. It will be understood, however, that the invention is not confined to the specific limitations set forth in the individual examples, but rather to the scope of the appended claims.

EXAMPLE I

A skin care lotion composition is prepared as follows: In a suitable vessel are combined 550.0 parts of purified water with 2.78 parts of Carbomer 941 (B.F. Goodrich's tradename for a thickener comprising a polymer of acrylic acid crosslinked with allyl sucrose), with vigorous stirring, until dispersal is complete. The mixture is then heated and the following ingredients are added:

37.08 parts propylene glycol, 9.25 parts isopropyl palmitate, 11.56 parts white oleic acid, 7.4 parts sorbitan stearate, 4.6 parts cetyl alcohol, 4.6 parts stearyl alcohol, 4.6 parts synthetic beeswax, 11.6 parts glyceryl monostearate, 11.6 parts stearic acid, 9.25 parts dimethicone (50 cstk) and 9.25 parts silicone wax. When the temperature of the mixture reaches 160° F., 1.5 parts methylparaben, 1.0 parts propylparaben, 0.5 parts butylparaben and 0.2 parts butylated hydroxytoluene are added, followed by 11.6 parts of premelted polyoxyethylene (4) sorbitan stearate (available from ICI under the tradename Polysorbate 61) and 13.9 parts of premelted myristyl myristate. A slurry composed of 75 parts of talc and 2.0 parts titanium dioxide in 166.75 parts of water, preheated to 180° F. is then added to the mixture. The temperature of the batch is brought to 180° F. and stirring is maintained for ten minutes. At this time, a solution of 1.20 parts sodium hydroxide in 50 parts of water is slowly added and stirring is continued for fifteen minutes at 180° F. Cooling of the mixture is then started. When the temperature reaches 120° F., 2.78 parts benzyl alcohol and 2.0 parts fragrance are added.

The resulting skin care composition has the following formulation:

|  | % wt/wt |
| --- | --- |
| talc | 7.50 |
| Carbomer 941 | 0.28 |
| propylene glycol | 3.71 |
| isopropyl palmitate | 0.93 |
| dimethicone (50 cstk) | 0.93 |
| white oleic acid | 1.16 |
| silicone wax | 0.93 |
| sorbitan stearate | 0.74 |
| cetyl alcohol | 0.46 |
| stearyl alcohol | 0.46 |
| synthetic beeswax | 0.46 |
| glyceryl stearate | 1.16 |
| stearic acid | 1.16 |
| Polysorbate 61 | 1.16 |
| myristyl myristate | 1.39 |
| methylparaben | 0.15 |
| propylparaben | 0.10 |

-continued

|  | % wt/wt |
| --- | --- |
| butylparaben | 0.05 |
| butylated hydroxytoluene | 0.02 |
| sodium hydroxide | 0.12 |
| titanium dioxide | 0.20 |
| benzyl alcohol | 0.28 |
| fragrance | 0.20 |
| water q.s. to | 100 |

The composition is a white lotion with desirable aesthetic and physical characteristics and the total weight % of non-volatile materials in this composition is 15.60 and the ratio of the non-volatile to talc is 2.08:1.

EXAMPLE II

A skin care lotion composition is prepared in accordance with the procedure of Example I and has the following formulation:

|  | % wt/wt |
| --- | --- |
| talc | 15.00 |
| Carbomer 941 | 0.26 |
| propylene glycol | 3.40 |
| isopropyl palmitate | 0.85 |
| dimethicone (50 cstk) | 0.85 |
| white oleic acid | 1.06 |
| silicone wax | 0.85 |
| sorbitan stearate | 0.68 |
| cetyl alcohol | 0.43 |
| stearyl alcohol | 0.43 |
| synthetic beeswax | 0.43 |
| glyceryl stearate | 1.06 |
| stearic acid | 1.08 |
| Polysorbate 61 | 1.08 |
| myristyl myristate | 1.28 |
| methylparaben | 0.15 |
| propylparaben | 0.10 |
| butylparaben | 0.05 |
| butylated hydroxytoluene | 0.02 |
| sodium hydroxide | 0.11 |
| benzyl alcohol | 0.26 |
| fragrance | 0.20 |
| water q.s. to | 100 |

The composition is a white, opaque lotion with desirable aesthetic and physical characteristics and the total weight % of non-volatile materials in this composition is 14.34 and the ratio of the non-volatiles to talc is 0.96:1.

EXAMPLE III

A skin care lotion composition is prepared in accordance with the procedure of Example I and has the following formulation:

|  | % wt/wt |
| --- | --- |
| talc | 30.00 |
| Carbomer 941 | 0.21 |
| propylene glycol | 2.80 |
| isopropyl palmitate | 0.70 |
| dimethicone (50 cstk) | 0.70 |
| white oleic acid | 0.88 |
| silicone wax | 0.70 |
| sorbitan stearate | 0.56 |
| cetyl alcohol | 0.35 |
| stearyl alcohol | 0.35 |
| synthetic beeswax | 0.35 |
| glyceryl stearate | 0.88 |
| stearic acid | 0.88 |
| Polysorbate 61 | 0.88 |
| myristyl myristate | 1.05 |
| methylparaben | 0.15 |
| propylparaben | 0.10 |

| | % wt/wt |
|---|---|
| butylparaben | 0.05 |
| butylated hydroxytoluene | 0.02 |
| sodium hydroxide | 0.09 |
| benzyl alcohol | 0.21 |
| fragrance | 0.20 |
| water q.s. to | 100 |

This composition is an off-white viscous lotion with desirable aesthetic and physical characteristics and the total weight % of non-volatile materials in this composition is 11.79 and the ratio of the non-volatile to talc is 0.39:1.

EXAMPLE IV

A skin care lotion composition is prepared in accordance with the procedure of Example I and has the following formulation:

| | % wt/wt |
|---|---|
| talc | 5.00 |
| Carbomer 941 | 0.29 |
| propylene glycol | 3.81 |
| isopropyl palmitate | 0.96 |
| dimethicone (50 cstk) | 0.96 |
| white oleic acid | 1.19 |
| silicone wax | 0.96 |
| sorbitan stearate | 0.76 |
| cetyl alcohol | 0.47 |
| stearyl alcohol | 0.47 |
| synthetic beeswax | 0.47 |
| glyceryl stearate | 1.19 |
| steric acid | 1.19 |
| Polysorbate 61 | 1.19 |
| myristyl myristate | 1.43 |
| methylparaben | 0.15 |
| propylparaben | 0.10 |
| butylparaben | 0.05 |
| butylated hydroxytoluene | 0.02 |
| sodium hydroxide | 0.12 |
| benzyl alcohol | 0.29 |
| fragrance | 0.20 |
| water q.s. to | 100 |

The resulting composition is a white lotion with desirable aesthetic and physical characteristics and the total weight % of non-volatile materials in this composition is 16.02 and the ratio of the non-volatiles to talc is 3.2:1.

EXAMPLE V

A skin care lotion composition is prepared as follows: In a suitable vessel are combined 599.9 parts of purified water with 2.8 parts of Carbomer 934 with vigorous stirring, until dispersal is complete. This mixture is then heated and the following ingredients are added: 36 parts propylene glycol, 9.0 parts isopropyl palmitate, 11.25 parts white oleic acid, 7.2 parts sorbitan stearate, 4.5 parts cetyl alcohol, 4.5 parts stearyl alcohol, 4.5 parts synthetic beeswax, 11.25 parts glyceryl monostearate and 11.25 parts stearic acid. When the temperature of the mixture reaches 160° F., 1.5 parts methylparaben, 1.0 parts propylparaben, 0.5 parts butylparaben and 0.2 parts BHT are added, followed by 10.8 parts of premelted polyoxyethylene (4) sorbitan stearate and 13.5 parts premelted myristyl myristate. A slurry composed of 100 parts talc and 2.0 parts titanium dioxide in 112.3 parts of water, preheated to 180° F. is then added to the mixture. The temperature of the batch is brought to 180° F. and stirring is maintained for ten minutes. At this time, a solution of 1.17 parts sodium hydroxide in 50 parts of water is slowly added and stirring is continued for fifteen minutes at 180° F. Cooling of the mixture is then started. When the temperature reaches 120° F., 3.0 parts benzyl alcohol and 1.6 parts fragrance are added.

The resulting composition has the following formulation:

| | % wt/wt |
|---|---|
| talc | 10.00 |
| isopropyl palmitate | 0.90 |
| Polysorbate 61 | 1.13 |
| sorbitan stearate | 0.72 |
| myristyl myristate | 1.35 |
| cetyl alcohol | 0.45 |
| stearyl alcohol | 0.45 |
| synthetic beeswax | 0.45 |
| glyceryl stearate | 1.13 |
| white oleic acid | 1.13 |
| stearic acid | 1.13 |
| propylene glycol | 3.60 |
| methylparaben | 0.15 |
| propylparaben | 0.10 |
| butylparaben | 0.05 |
| butylated hydroxytoluene | 0.02 |
| Carbomer 934 | 0.28 |
| titanium dioxide | 0.20 |
| sodium hydroxide | 0.12 |
| fragrance | 0.16 |
| benzyl alcohol | 0.30 |
| water q.s. to | 100 |

The resulting composition is a white, viscous lotion with desirable aesthetic and physical characteristics and the total weight % of non-volatile materials in this composition is 13.42 and the ratio of the non-volatiles to talc is 1.34:1.

EXAMPLE VI

A skin care lotion composition is prepared in accordance with the procedure of Example V and has the following formulation:

| | % wt/wt |
|---|---|
| talc | 15.00 |
| isopropyl plamitate | 0.85 |
| Polysorbate 61 | 1.06 |
| sorbitan stearate | 0.68 |
| myristyl myristate | 1.28 |
| cetyl alcohol | 0.43 |
| stearyl alcohol | 0.43 |
| synthetic beeswax | 0.43 |
| glyceryl stearate | 1.06 |
| white oleic acid | 1.06 |
| stearic acid | 1.06 |
| propylene glycol | 3.40 |
| methylparaben | 0.15 |
| propylparaben | 0.10 |
| butylparaben | 0.05 |
| butylated hydroxytoluene | 0.02 |
| Carbomer 934 | 0.26 |
| sodium hydroxide | 0.11 |
| fragrance | 0.16 |
| benzyl alcohol | 0.26 |
| water q.s. to | 100 |

The resulting composition is a white, opaque, free-flowing lotion with desirable aesthetic and physical characteristics. The total weight % of non-volatile materials in this composition is 12.63 and the ratio of the non-volatiles to talc is 0.84:1.

In order to demonstrate that the skin care compositions prepared in accordance with the present invention have improved physical characteristics, the following test procedure is followed. A "paired comparison" evaluation procedure in accordance with the Manual on Sensory Testing Methods, ASTM Special Technical Publication 434, is carried out by placing 0.4 ml of the lotion composition of Example VI and 0.4 ml of the same lotion without the 15% talc a distance apart on the same arm of a test subject. The arm is previously cleaned, dried and void of any other product, and the test samples are applied by an experienced Sensory Technician. Various evaluative questions are asked and answered and then the subject is asked to spread the lotions over the skin and additional questions are asked and answered. Thereafter, the lotions are further rubbed in and still more questions are asked and answered. The subjects are unaware of any details regarding the test samples.

When the above tests are carried out with the composition of Example VI and a composition containing the same ingredients except for the presence of talc, the skin care composition of Example VI is perceived to be distinct from the other composition. Further, the test subjects prefer the composition of Example VI and perceive it to result in "softer, smoother skin".

EXAMPLE VII

A skin care lotion composition is prepared in accordance with the procedure of Example V and has the following formulation:

|  | % wt/wt |
| --- | --- |
| talc | 20.00 |
| isopropyl palmitate | 0.80 |
| Polysorbate 61 | 1.00 |
| sorbitan stearate | 0.64 |
| myristyl myristate | 1.20 |
| cetyl alcohol | 0.40 |
| stearyl alcohol | 0.40 |
| synthetic beeswax | 0.40 |
| glyceryl stearate | 1.00 |
| white oleic acid | 1.00 |
| stearic acid | 1.00 |
| propylene glycol | 3.20 |
| methylparaben | 0.15 |
| propylparaben | 0.10 |
| butylparaben | 0.05 |
| butylated hydroxytoluene | 0.02 |
| Carbomer 934 | 0.24 |
| sodium hydroxide | 0.10 |
| benzyl alcohol | 0.24 |
| fragrance | 0.16 |
| water q.s. to | 100 |

The resulting composition is a white lotion with desirable aesthetic and physical characteristics. The total weight % of non-volatile materials in this composition is 11.88, and the ratio of non-volatiles to talc is 0.59:1.

EXAMPLE VIII

A baby cream skin care composition is prepared in accordance with the procedure of Example V and has the following formulation:

|  | % wt/wt |
| --- | --- |
| talc | 30.00 |
| mineral oil | 25.76 |
| white wax | 5.60 |
| synthetic beeswax | 4.90 |
| ceresine wax | 4.83 |
| lanolin | 3.92 |
| paraffin | 3.01 |

-continued

|  | % wt/wt |
| --- | --- |
| dimethicone (50 cstk) | 1.40 |
| glyceryl stearate/polyethylene glycol (100) stearate | 0.70 |
| sodium borate | 0.63 |
| propylparaben | 0.14 |
| fragrance | 0.11 |
| water q.s. to | 100 |

The resulting composition is a white cream with desirable aesthetic and physical characteristics and the total weight % of non-volatile materials is 50.89, and the ratio of non-volatiles to talc is 1.70:1.

EXAMPLE IX

An anhydrous skin care composition is prepared as follows: In a suitable vessel is placed 250 parts petrolatum which is heated to 95° C. 15.0 parts Polyethylene AC617A (Allied Corporation's tradename for powdered polyethylene) is added with vigorous stirring. 0.5 parts propylparaben is then added and the mixture stirred until homogeneous. In a separate vessel are combined 50 parts dimethicone (50 cstk), 169 parts cyclomethicone, 5 parts mineral oil and 10 parts Cabosil M-5 (fumed silica) and the mixture heated to 60° C. and mixed until homogeneous. This mixture is then added with stirring to the petrolatum mixture and 500 parts of talc and 0.5 parts fragrance are added, and the mixture is cooled.

The resulting anhydrous composition has the following formulation:

|  | % wt/wt |
| --- | --- |
| talc | 50.00 |
| petrolatum | 25.00 |
| powdered polyethylene | 1.50 |
| cyclomethicone | 16.90 |
| dimethicone (50 cstk) | 5.00 |
| mineral oil | 0.50 |
| Cabosil M-5 | 1.00 |
| propylparaben | 0.05 |
| fragrance | 0.05 |

The resulting composition has desirable aesthetic and physical characteristics and the total weight % of non-volatile materials in this viscous composition is 33.05 and the ratio of non-volatiles to talc is 0.66:1.

EXAMPLE X

An anhydrous skin care composition is prepared in accordance with the procedure of Example IX and has the following formulation:

|  | % wt/wt |
| --- | --- |
| talc | 40.00 |
| petrolatum | 30.00 |
| powdered polyethylene | 1.80 |
| cyclomethicone | 20.28 |
| dimethicone (50 cstk) | 6.00 |
| mineral oil | 0.60 |
| Cabosil M-5 | 1.20 |
| propylparaben | 0.06 |
| fragrance | 0.06 |

The resulting composition has desirable aesthetic and physical characteristics and the total weight % of non-volatile materials in this combination is 38.66 and the ratio of non-volatiles to talc is 0.97:1.

EXAMPLE XI

A market research study is conducted as follows: Numerous screenings are undertaken on a random door-to-door basis to identify women in the age bracket of from 18 to 49 who use a hand and body lotion at least three times a week. This screening is conducted until a panel of about 100 subjects is obtained. The panel is then individually exposed to an unidentified concept describing the compositions of the present invention, and they are questioned about it. If their attitudes are not negative towards such a product, based on its description, each individual is then given an unidentified container of the product of Example V for personal use for a period of two weeks. At the end of the two-week period, a personal call-back is conducted to obtain reactions to the product, and also at that time, any remaining product is retrieved and the women are then given a second unidentified product which is a commercially available hand and body lotion to use under the same circumstances for the following two weeks. After the second two-week usage period, a telephone call-back is conducted to obtain reactions to the commercial product as well as to preference between the two products. The results are then rated monadically. The overall rating for the composition of Example V on a scale of 0 to 100 was 76 while the rating for the commercial product was only 64, which is a significant difference. When the two products were compared with each other, the composition of Example V had a significant win, i.e., 78% to 22%, of those women who expressed a preference of the composition of Example v was that it is perceived to be less or not greasy on the skin and to leave the skin feeling soft and smooth.

The above results clearly demonstrate that the compositions of the present invention exhibit significantly enhanced aesthetic and physical characteristics compared to commercially available products as well as when compared to the same formulations not containing talc.

Various other features and embodiments of the present invention not specifically enumerated will be obvious to those skilled in the art, all of which may be achieved without departing from the spirit and the scope of the invention as defined by the following claims.

What is claimed is:

1. A skin care composition comprising a lotion, cream or anhydrous base containing non-volatile oils and waxes and talc wherein the ratio of the non-volatile ingredients to talc is from about 0.4:1 to 3.2:1.

2. The skin care composition of claim 1, wherein the ratio of the non-volatile ingredients to talc is from about 0.6:1 to 2.0:1.

3. The skin care composition of claim 1, wherein the ratio of the non-volatile ingredients to talc is from about 1.0:1 to 1.4:1.

4. The skin care composition of claim 1, wherein the base is a lotion.

5. The skin care composition of claim 1, wherein the base is a cream.

6. The skin care composition of claim 1, wherein the base is an anhydrous base.

7. The skin care composition of claim 1, wherein the talc has a particle size such that 100% passes through a 60 mesh screen and not less than 99% passes through a 100 mesh screen and at least 98% passes through a 200 mesh screen.

8. A method for treating the skin comprising topically applying an effective amount of a skin care composition to the skin wherein the skin care composition comprises a lotion, cream or anhydrous base containing non-volatile oils and waxes and talc wherein the ratio of the non-volatile ingredients to talc is from about 0.4:1 to 3.2:1.

* * * * *